(12) United States Patent
Bommarito et al.

(10) Patent No.: US 12,251,489 B2
(45) Date of Patent: Mar. 18, 2025

(54) STERILIZATION CHEMICAL INDICATOR

(71) Applicant: Solventum Intellectual Properties Company, Maplewood, MN (US)

(72) Inventors: G. Marco Bommarito, Stillwater, MN (US); Scott D. Anderson, Lakeland, MN (US); Ryan W. Clarke, Woodbury, MN (US); Paul N. Holt, St. Paul, MN (US); William E. Foltz, Cottage Grove, MN (US); Timothy J. Nies, Stillwater, MN (US); Kevin D. Landgrebe, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 947 days.

(21) Appl. No.: 17/309,515

(22) PCT Filed: Dec. 19, 2019

(86) PCT No.: PCT/IB2019/061110
§ 371 (c)(1),
(2) Date: Jun. 3, 2021

(87) PCT Pub. No.: WO2020/128956
PCT Pub. Date: Jun. 25, 2020

(65) Prior Publication Data
US 2022/0054692 A1    Feb. 24, 2022

Related U.S. Application Data

(60) Provisional application No. 62/783,764, filed on Dec. 21, 2018.

(51) Int. Cl.
*A61L 2/28* (2006.01)
*A61L 2/07* (2006.01)
*G01N 33/52* (2006.01)

(52) U.S. Cl.
CPC ............ *A61L 2/28* (2013.01); *A61L 2/07* (2013.01); *G01N 33/525* (2013.01); *A61L 2202/14* (2013.01); *A61L 2202/24* (2013.01)

(58) Field of Classification Search
CPC .......... A61L 2/07; A61L 2/28; A61L 2202/14; A61L 2202/24; G01N 33/525
See application file for complete search history.

(56) References Cited

U.S. PATENT DOCUMENTS

| | | |
|---|---|---|
| 4,138,216 A | 2/1979 | Larsson |
| 4,410,493 A | 10/1983 | Joslyn |

(Continued)

FOREIGN PATENT DOCUMENTS

| | | | |
|---|---|---|---|
| EP | 202724 A | * 11/1986 | ............ A61L 2/28 |
| EP | 0428245 | 5/1991 | |

(Continued)

OTHER PUBLICATIONS

International Search Report for PCT International Application No. PCT/IB2019/061110, mailed on Jun. 25, 2020, 6 pages.

*Primary Examiner* — Jennifer Wecker

(57) ABSTRACT

The present disclosure relates generally to chemical indicators. In particular, the chemical indicators are useful for monitoring sterilization processes. The chemical indicator includes a fluid pathway and a chamber comprises a chemical-indicating composition.

14 Claims, 5 Drawing Sheets

(56) References Cited

U.S. PATENT DOCUMENTS

| | | | |
|---|---|---|---|
| 4,579,715 A | | 4/1986 | Bruso |
| 5,217,901 A | * | 6/1993 | Dyckman ................. A61L 2/28 |
| | | | 435/31 |
| 5,872,004 A | | 2/1999 | Bolsen |
| 6,485,979 B1 | | 11/2002 | Kippenhan |
| 6,897,059 B2 | | 5/2005 | Foltz |
| 7,045,343 B2 | | 5/2006 | Witcher |
| 7,247,482 B2 | | 7/2007 | Lemus |
| 7,481,975 B2 | | 1/2009 | Read |
| 7,927,866 B2 | | 4/2011 | Justi |
| 9,017,994 B2 | | 4/2015 | Franciskovich |
| 11,065,354 B2 | * | 7/2021 | Hajime et al. ............ A61L 2/28 |
| | | | 116/219 |
| 2003/0215923 A1 | | 11/2003 | Witcher |
| 2008/0261296 A1 | * | 10/2008 | Justi ......................... A61L 2/28 |
| | | | 435/287.4 |
| 2013/0168327 A1 | * | 7/2013 | Clark ..................... G01N 21/78 |
| | | | 210/749 |

FOREIGN PATENT DOCUMENTS

| | | |
|---|---|---|
| EP | 2362786 | 9/2011 |
| JP | 2003159649 A | 6/2003 |
| JP | 2015512620 A | 4/2015 |
| JP | 2018516105 A | 6/2018 |
| WO | WO 2002-087639 | 11/2002 |
| WO | 2013122852 A1 | 8/2013 |
| WO | 2016/164329 A1 | 10/2016 |
| WO | 2018106860 A1 | 6/2018 |
| WO | WO 2020-217093 | 10/2020 |

* cited by examiner

STERILIZATION CHEMICAL INDICATOR

CROSS REFERENCE TO RELATED APPLICATIONS

This application is a national stage filing under 35 U.S.C. 371 of PCT/IB2019/061110, filed Dec. 19, 2019, which claims the benefit of U.S. Provisional Application No. 62/783,764 filed Dec. 21, 2018, the disclosure of which is incorporated by reference in its/their entirety herein.

The present disclosure relates generally to chemical indicators for monitoring sterilization processes.

BACKGROUND

Medical instruments, particularly surgical instruments, are typically sterilized prior to use using steam or other sterilizing gases or liquids. A commonly used sterilization process is exposure of the instruments to steam under pressure. Alternative sterilization processes use gasses such as ethylene oxide and hydrogen peroxide as the sterilant. The use of hydrogen peroxide and other chemical vapor-phase sterilization techniques typically involves operating temperatures well below those associated with steam sterilization, and is, therefore, suitable for temperature-sensitive devices, such as those comprising plastics.

Sterilization indicators are used to monitor whether a sterilization process has been performed and/or whether critical sterilization parameters have been met. Sterilization indicators typically include a chemical-indicating composition, carried on a substrate, which changes color during the sterilization process. Sterilization process indicators show whether the monitored instruments and devices have been exposed to a sterilant, regardless of the exposure time. Sterilization integrators, on the other hand, show whether the monitored instruments and devices have been exposed sufficiently to sterilant to meet more than one of the critical parameters for sterilization (typically time of exposure to sterilant, concentration of sterilant, and temperature of sterilant).

For gaseous sterilants other than steam, such as hydrogen peroxide and ethylene oxide, design of an indicator is made difficult by the tendency of those gasses to penetrate and then slowly diffuse out of the materials of the indicator and the medical device being sterilized. The sequestration and subsequent slow outgassing of sterilant may cause the indicator to continue to change color even after the sterilization process is complete. For hydrogen peroxide sterilization indicator design, an additional factor that comes into play is the high oxidizing power of hydrogen peroxide, which may cause the color of the indicator to change too quickly to make it useful for monitoring critical parameters of sterilization as needed for a sterilization integrator. Furthermore, as surgical instruments and medical devices become more complex, there is a continuing need for monitoring sterilization of lumened instruments and of hard-to-reach surfaces of complex devices. The present disclosure provides solutions to these problems and needs that have been recognized by investigators in the field of sterilization monitoring.

SUMMARY

Generally, the present disclosure relates to chemical indicators. More particularly, the present disclosure relates to chemical indicators useful for monitoring sterilization processes. The chemical indicator includes a fluid pathway and a chamber comprises a chemical-indicating composition.

In one embodiment, the chemical indicators of the disclosure comprise:
 a first sheet;
 a second sheet positioned in an overlapping relationship with respect to the first sheet;
 a third sheet positioned between the first sheet and the second sheet;
 a fluid pathway; and
 a chamber;
 wherein the fluid pathway comprises a bottom portion, a top portion, and two side portions;
 wherein the chamber comprises a chemical-indicating composition;
 wherein the bottom portion of the fluid pathway is defined by the first sheet, the top portion of the fluid pathway is defined by the second sheet, and the sides of the fluid pathway are defined by the third sheet, the fluid pathway having a first end that defines a first opening and a second end that defines a second opening;
 wherein a first end of the fluid pathway is configured to be in fluid communication with ambience and the second end of the fluid pathway is configured to be in fluid communication with the chamber.

See FIG. 1 for a schematic representation of certain aspects of the embodiment described above.

In some embodiments, the first sheet and the second sheet are substantially impermeable to sterilant.

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure.

Unless otherwise indicated, all numbers in the description and the claims expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The recitation of numerical ranges by endpoints includes all numbers subsumed within that range (e.g. a range from 1 to 5 includes, for instance, 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "substantially impermeable" as used herein refers to the relative inability of sterilant gas to penetrate a sheet of the chemical indicator. The goal of using substantially impermeable material is to prevent the transport of sterilant, such as hydrogen peroxide, across the material so that sterilant is only transported via the opening and corresponding channel to the chemical-indicating composition. In some embodiments, the material allows transport of sterilant across a sheet of less than 5% of the sterilant flowing across the opening during the sterilization cycle. In other embodiments, the material allows transport of sterilant across a sheet of less than 1%, or less than 0.5%, or less than 0.1% of the sterilant flowing across the opening during the sterilization cycle. An indicator of the present disclosure comprising substantially impermeable first and second sheets allows sterilant gas to move along the fluid pathway and contact the chemical-indicating composition and does not allow sterilant gas to contact the chemical-indicating composition by traversing the first and second sheets. As such, a test for substantial impermeability of a sheet of the disclosure can be made by blocking entrance of sterilant gas to the opening(s) of the fluid pathway(s) of the indicator of the present disclosure; if the color of the indicator changes by exposure of such a modified indicator to sterilant gas after completion of a sterilization cycle, then the sheets are not considered to be substantially impermeable for the purposes of the present disclosure.

The term "immediately adjacent" refers to the relative position of two elements such as, for example, two sheets or layers that are next to one another and in contact with one another and have no intermediate sheet or layer separating the two elements. The term "immediately adjacent," however, encompasses configurations in which one or both elements (e.g., sheets) have been treated with a primer, or whose surface has been modified otherwise to affect the properties thereof, such as by etching, by embossing, etc., or have been subjected to other surface treatments, such as corona or plasma treatments, etc. that may improve adhesion.

The term "substantially centrally" refers to a position located within two points A and B (e.g., the end openings of a fluid pathway) that is within 10% in distance, in any direction, from the geometrical middle point between the two points A and B.

The term "substantially circular" refers to the shape of an element A that can be circumscribed within the donut-shaped area resulting from subtracting the area of a circle X from the area of a circle Y, wherein the circle X has an area that is 10% smaller than the area of element A and circle Y has an area that is 10% larger than the area of element A. Circles X and Y are assumed to be concentric in this definition.

The term "substantially along the entire length" of an element (e.g., a fluid pathway) refers to a length that is within 10% of the total length of the element. For example, a chamber that extends substantially along the entire length of a fluid pathway refers to a chamber whose length is within 10% of the total length of the fluid pathway.

The term "modulate" or "modulates" in the context of the transport of a sterilant in a fluid pathway (by flow, diffusion, etc.) refers to the ability to decrease the transport of the sterilant in the fluid pathway, either in terms of reducing the mass of sterilant moving along the pathway, or reducing the speed of transport of the sterilant.

In the following description, reference is made to the accompanying figures herein described. In certain cases, the figures may depict, by way of illustration, several specific embodiments of the present disclosure. It is to be understood that other embodiments different from those explicitly depicted in the figures are contemplated and may be made without departing from the scope or spirit of the present disclosure. The following detailed description, therefore, is not to be taken in a limiting sense.

DETAILED DESCRIPTION

Figure 1:
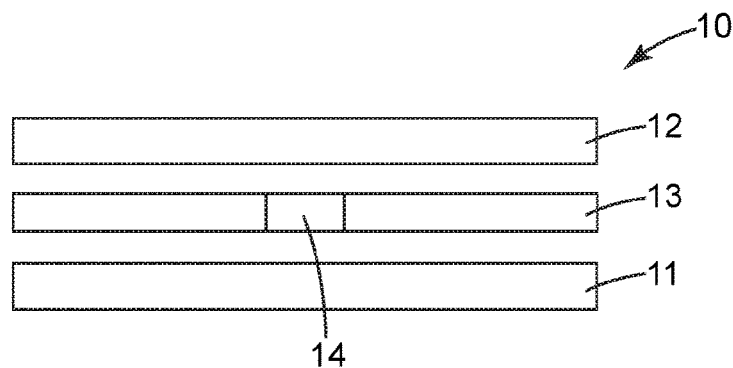
FIG. 1 is an exploded cross-sectional view of an embodiment of a chemical indicator of this disclosure.

Referring now to the drawings, FIG. 1 is an exploded cross-sectional view of an embodiment of the chemical indicator 10 of the present disclosure. The chemical indicator 10 comprises a first sheet 11, a second sheet 12, a third sheet 13, and a fluid pathway 14. Although FIG. 1 is an exploded view, one or ordinary skill in the art would understand that in an embodiment of a chemical indicator of the present disclosure based on FIG. 1 the first sheet is adjacent, or immediately adjacent, the third sheet and the third sheet is adjacent, or immediately adjacent, the second sheet. The first and second sheets define the bottom and top of the fluid pathway. In the embodiment shown, the third sheet comprises a cutaway or groove, or is, itself, created by placing two sheets proximally to one another. As shown in FIG. 1, the third sheet forms the side walls of the fluid pathway. Thus, in one embodiment, the fluid pathway is formed by the combination of the first, second, and third sheets. The fluid pathway 14 provides a conduit through which a sterilizing gas, such as hydrogen peroxide, steam, or ethylene oxide, moves during a sterilization cycle to a chamber that contains a chemical-indicating composition.

Figure 2:
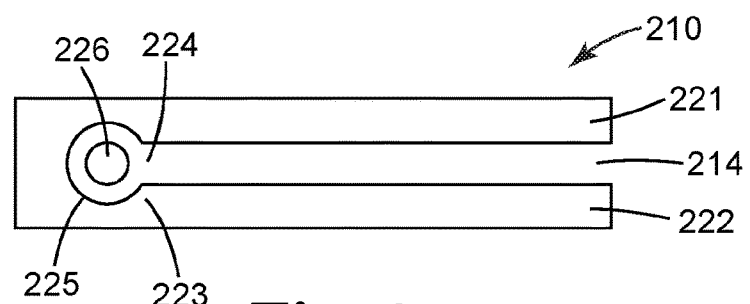
FIG. 2 is a top view of an embodiment of a chemical indicator of this disclosure.

FIG. 2 is a top view of an embodiment of the chemical indicator of this disclosure. In this view, the top sheet (closer to the observer) is assumed to be transparent so that sheet is visible. In this figure, the indicator dot is on the first or second sheet. As shown in FIG. 2, the chemical indicator 210 of the present disclosure has a first end 221 with a first opening 222 that is in fluid communication with ambience and a second end 223 with a second opening 224 that is in fluid communication with a chamber 225 that comprises a chemical-indicating composition 226. The first opening 222 and the second opening 224 each have a height H and a width W. The height H of the two openings 222 and 224 is the perpendicular distance at the openings between the first sheet and the second sheet, whereas the width W of the two openings 222 and 224 is the perpendicular distance at the openings between the side walls of the openings that are formed by the groove or cutaway in the third sheet. During use, sterilant gas enters the first opening 222, and then diffuses along the fluid pathway 214 and through the second opening 224 to a chamber 225, whereupon it reacts with the chemical-indicating composition 226.

Figure 3:
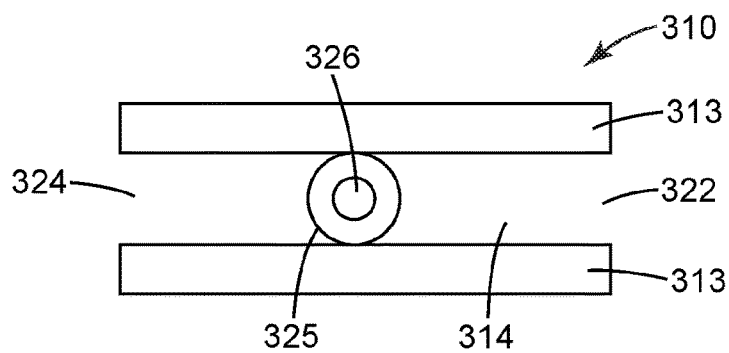
FIG. 3 is a top view of an embodiment of a chemical indicator of this disclosure.

FIG. 3 is a top view of an embodiment of the chemical indicator 310 of this disclosure. As shown in FIG. 3, the chemical indicator 310 of the present disclosure has a first opening 322 that is in fluid communication with ambience and chamber 325, and a second opening 324 that is in fluid communication with ambience and the same chamber 325 that is in fluid communication with the first opening 322. The first opening 322 and the second opening 324 each have a height H and a width W. The height H of the two openings 322 and 324 is the perpendicular distance at the openings between the first sheet and the second sheet, whereas the width W of the two openings 322 and 324 is the perpendicular distance at the openings between the side walls of the openings that are formed by the groove or cutaway in the third sheet. The chamber comprises a chemical-indicating composition 326. During use, sterilant gas enters the first and second openings 322 and 324, and then diffuses along the fluid pathway 314 and to the chemical-indicating composition 326 contained on or within chamber 325, whereupon it reacts with the chemical-indicating composition 326.

Figure 4:
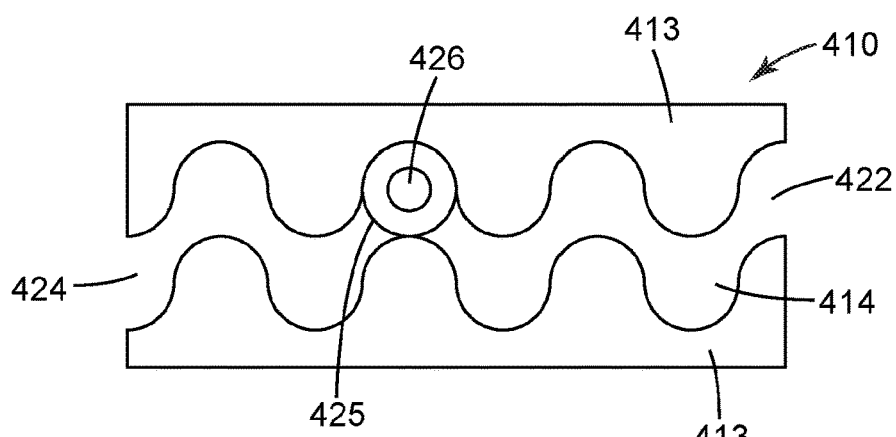
FIG. 4 is a top view of an embodiment of a chemical indicator of this disclosure.

FIG. 4 is a top view of an embodiment of the chemical indicator 410 of this disclosure. As shown in FIG. 4, the chemical indicator 410 has a first opening 422 and a second opening 424 that are in fluid communication via a tortuous fluid pathway 414 with a chemical-indicating composition 426 that is situated on or within chamber 425. During use, sterilant gas enters the first and second openings 422 and 424, and then diffuses along the tortuous fluid pathway 414 and to the chemical-indicating composition 426 contained on or within chamber 425, whereupon it reacts with the chemical-indicating composition 426. The first opening 422 and the second opening 424 each have a height H and a width W. The height H of the two openings 422 and 424 is the perpendicular distance at the openings between the first sheet and the second sheet, whereas the width W of the two openings 422 and 424 is the perpendicular distance at the openings between the side walls of the openings that are formed by the groove or cutaway in the third sheet.

Figure 5:
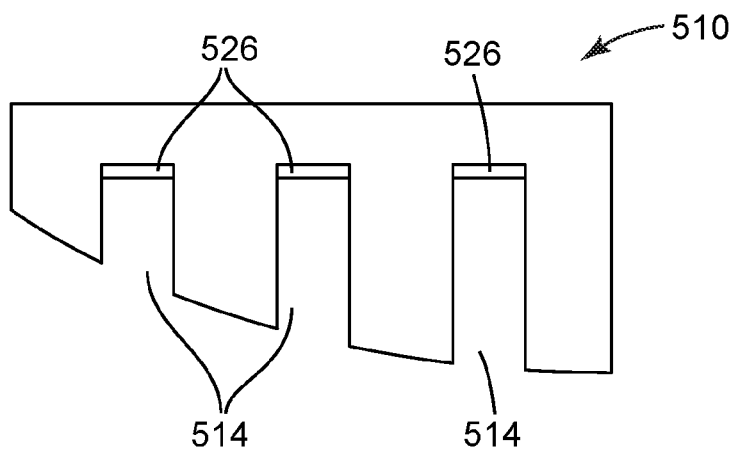
FIG. 5 is a top view of an embodiment of a chemical indicator of this disclosure.

FIG. 5 is a top view of an embodiment of the chemical indicator 510 of this disclosure. As shown in FIG. 5, the chemical indicator 510 comprises multiple fluid pathways 514 and multiple chemical-indicating compositions 526. During use, sterilant gas enters and diffuses along each of the multiple fluid pathways 514 to the multiple chemical-indicating compositions 526, whereupon it reacts with the chemical-indicating compositions 526. Each of the fluid pathways 514 of this embodiment of the chemical indicator 510 of the present disclosure may have a length that is different from the lengths of every other of the fluid pathways 514. Thus, each of the chemical-indicating compositions 526, which are in fluid communication with ambience via the multiple fluid pathways 514, may change color after different lengths of exposure time to the sterilant.

Figure 6:
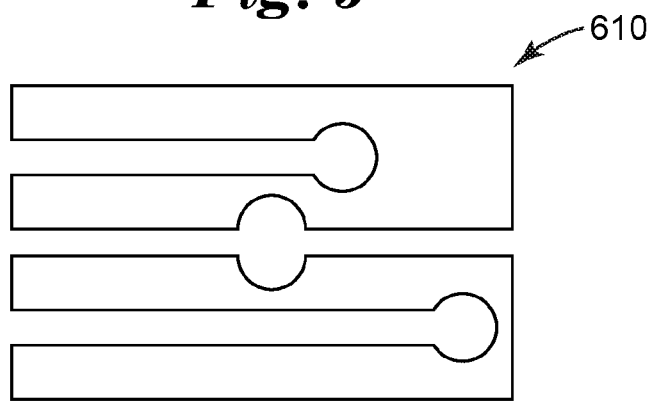
FIG. 6 is a top view of an embodiment of a chemical indicator of this disclosure.

FIG. 6 is a top view of an embodiment of the chemical indicator 610 of this disclosure. As shown in FIG. 6, the chemical indicator 610 is an array of fluid pathways, each in fluid communication with ambience and a chemical-indicating composition. The array enables customization of each component to be responsive to a sterilant gas at a specific set of sterilization parameters. As such, the chemical indicator 610 may be suitable for monitoring a number of different sterilization protocols.

Figure 7:
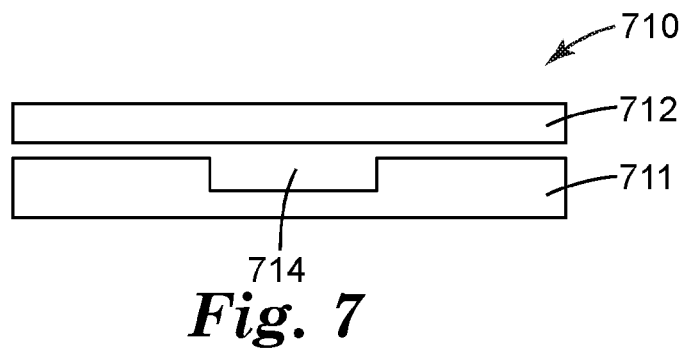
FIG. 7 is a cross-sectional view of an embodiment of a chemical indicator of this disclosure.

FIG. 7 is a cross-sectional view of an embodiment of the chemical indicator 710 of the present disclosure. The chemical indicator 710 comprises a first sheet 711, a second sheet 712, and a fluid pathway 714. The first sheet 711 defines the bottom of the fluid pathway and, in the embodiment shown, comprises a cutaway or groove forming the side walls of the fluid pathway. The second sheet 712 defines the top of the fluid pathway. Thus, the fluid pathway 714 is integrated with the first sheet 711. The fluid pathway 714 provides a conduit through which a sterilizing gas, such as hydrogen peroxide, steam, or ethylene oxide, moves during a sterilization cycle to a chamber that contains a chemical-indicating composition.

Figure 8:
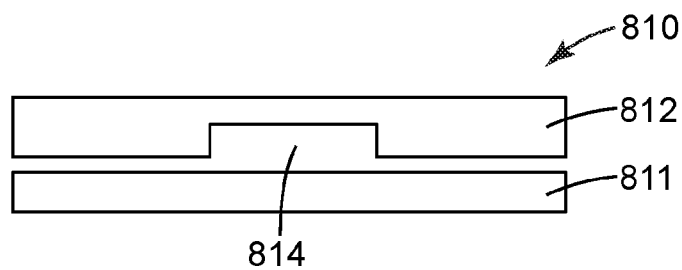
FIG. 8 is a cross-sectional view of an embodiment of a chemical indicator of this disclosure.

FIG. 8 is a cross-sectional view of an embodiment of the chemical indicator 810 of the present disclosure. The chemical indicator 810 comprises a first sheet 811, a second sheet 812, and a fluid pathway 814. The first sheet 811 defines the bottom of the fluid pathway 814. The second sheet 812 defines the top of the fluid pathway and, in the embodiment shown, comprises a cutaway or groove forming the side walls of the fluid pathway. Thus, the fluid pathway 814 is integrated with the second sheet 812. The fluid pathway 814 provides a conduit through which a sterilizing gas, such as hydrogen peroxide, steam, or ethylene oxide, moves during a sterilization cycle to a chamber that contains a chemical-indicating composition.

Figure 9:
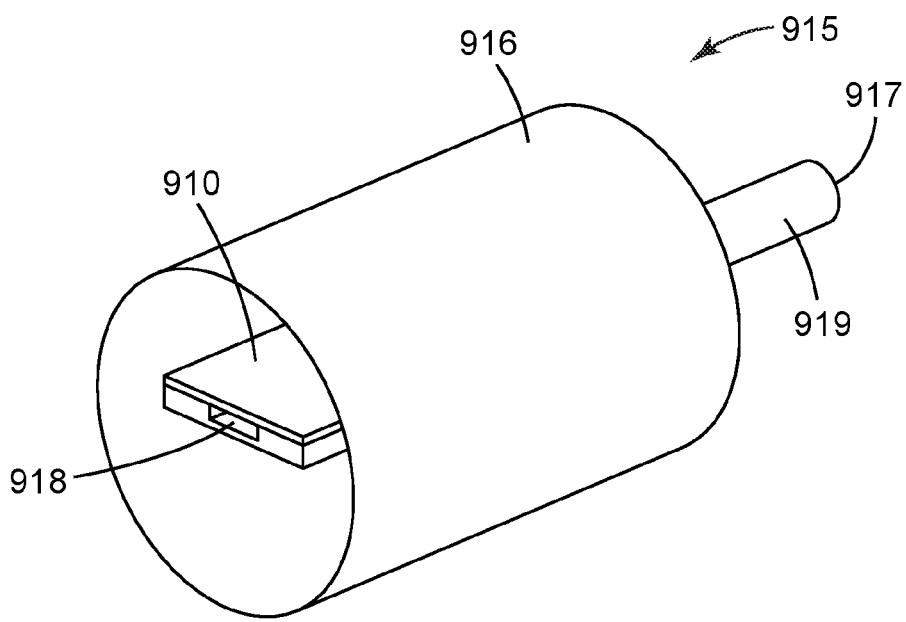
FIG. 9 is a perspective view of a chemical indicator-comprising process challenge device of this disclosure.

FIG. 9 is a perspective view of a chemical indicator-comprising process challenge device of this disclosure. The process challenge device 915 comprises a container 916 with its own fluid pathway, which provides fluid communication between ambience and the internal contents of the container 916 via a first opening 917, and, optionally, a second opening 918. The container 916 contains a chemical indicator 910. In use, sterilant gas passes into the first opening 917, through the chemical indicator 910, and out of the second opening 918. The process challenge device 915 may comprise a constriction 919 that restricts flow of gasses through the container 916.

As stated previously, the chemical indicator of the present disclosure comprises a first sheet, a second sheet, and a third sheet. Such sheets may be formed from virtually any material that can be made in sheet form. For example, the sheets may be formed from paper, from a polymeric material such as a plastic film, or from a metal foil, etc., and the individual sheets may be formed from materials different from one another. To be suitable for use for detecting the change in color of the chemical-indicating composition of the indicator, at least one of the first and second sheets desirably has some transparency or translucency to be able to observe a color change on the indicator. In some embodiments, at least one of the first and second sheets must be sufficiently translucent or transparent to observe the color of the indicator. For use of the indicator to monitor hydrogen peroxide sterilization processes, the sheets are preferably formed from materials other than paper, and from materials that do not retain large amounts of hydrogen peroxide. Particularly suitable materials from which sheets of the present disclosure may be formed include polyester, vinyl rubber, EPDM rubber, polyethylene, polypropylene, and polystyrene. Preferably, the chemical-indicating composition reacts only with sterilant that reaches the chemical-indicating composition by diffusing along the fluid pathway. In one embodiment, at least the first and second sheets should be substantially impermeable to sterilant The sheets of the chemical indicator of the present disclosure may be adhered to one another by laminating the sheets to one another using heat and pressure using a laminator. Alternatively, the sheets may be adhered to one another using an adhesive. Preferably, the adhesive should prevent delamination of the three sheets during use and should not interact adversely with sterilant to affect the color change of the chemical-indicating composition. Acceptable adhesives for adhering the sheets to one another include natural adhesives, such as rubber-based adhesives, and synthetic adhesives, such as synthetic rubber adhesive, acrylic adhesives, silicone adhesives, etc.

As stated previously, the third sheet of the chemical indicator forms the sides of the fluid pathway. In some preferred embodiments, the third sheet may contain a groove or cutaway region. Alternatively, the third sheet is, itself, formed from two sheets placed proximal to one another. In this embodiment, the third sheet comprises two substantially coplanar sheets having sides that are separated from each other by a distance that is equal to the width W of the fluid pathway for at least a portion of the distance between them. If the third sheet contains a groove or cutaway region, the groove or cutaway region is fashioned by removing a partial-thickness region of the sheet (to create a groove) or a full-thickness region of the sheet (to create a cutaway region). The removal of a thickness of the sheet can be performed using a knife or other means of cutting, for example, by using a laser cutter. In some embodiments, the first and third sheets are a monolithic structure, and in some other embodiments the second and third sheets are a monolithic structure.

The fluid pathway of the chemical indicator of the present disclosure is formed from the overlapping of the first sheet, the second sheet, and the third sheet. The fluid pathway has a length L. The length L of the fluid pathway is any convenient length. In one embodiment, the fluid pathway has a length L of no longer that 10 cm. The fluid pathway has a first opening and a second opening, each of which has a height H and a width W. The height H of the two openings is the perpendicular distance at the openings between the first sheet and the second sheet, whereas the width W of the two openings is the perpendicular distance at the openings between the side walls of the openings that are formed by the groove or cutaway in the third sheet. In some embodiments, the aspect ratio is the ratio of the width to the height (W/H) of the two openings and should be at least 4 (4:1).

The height of the fluid pathway of the indicator is determined by the height of the third sheet, or alternatively by the distance between the first and second sheets if one or more additional layer is present that forms part of the sides of the fluid pathway and thus adds to the height of the fluid pathway. For indicator constructions comprising a third sheet that comprises a film layer and adhesive layers, the number of adhesive and film layers present in the indicator construction and their respective thicknesses determine the fluid pathway height. The height and width dimensions of the channel, along with the number of openings in the indicator, control the amount of sterilant vapor entering the indicator during the sterilization process.

The fluid pathway can provide to the indicator a process challenge functionality. For example, the tortuous fluid pathway shown in FIG. 4 provides a greater challenge to diffusion of sterilant along the fluid pathway to the chamber comprising a chemical-indicating composition than a linear fluid pathway provides. Other ways of constructing a fluid pathway to provide a process challenge include reducing the height and/or width of the first and/or second opening, treating the walls of the fluid pathway with a chemical that reacts with and degrades the sterilant, treating the walls with a chemical that absorbs and sequesters sterilant, incorporating a barrier material in the fluid pathway that reduces flow of sterilant along the pathway to the chemical-indicating composition, etc.

The chemical-indicating composition of the present disclosure may contain one fluid pathway or more than one fluid pathway. In some embodiments of the present disclosure, as shown in FIG. 2, the one fluid pathway is in fluid communication with ambience and a chamber that comprises a chemical-indicating composition. In other embodiments of the present disclosure, as shown in FIG. 3 and FIG. 4, each of the two fluid pathways is in fluid communication both with ambience and a centrally located chamber comprising a chemical-indicating composition. In other embodiments of the present disclosure, as shown in FIG. 5 and FIG. 6, each of several fluid pathways is in fluid communication with ambience and a chamber comprising a chemical-indicating composition.

The chemical-indicating composition of the indicator of the present disclosure may comprise one or more dye and pigment that changes from one color to another color (including from colorless to colored, or vice versa) upon interaction with the sterilant. For steam sterilant, a typical interaction of the indicator with the sterilant involves production of sulfur anions that react with lead or another metal to make a black metal sulfide. For ethylene oxide sterilant, a typical interaction of the indicator with sterilant involves reaction of a dye or pigment with ethylene oxide directly, which results in a color change. Another approach for indication of ethylene oxide involves use of an indicating composition that contains a metal salt, reaction of which with ethylene oxide results in a pH change that can be detected by a dye that is a pH indicator. For hydrogen peroxide sterilant, a typical interaction of the indicator with sterilant involves oxidation of the indicator dye or pigment. Another approach involves oxidation of a metal salt to make highly reactive oxygen radicals that subsequently react with the dye or pigment. The chemical-indicating composition of the present disclosure may contain more than one dye or pigment, or a mixture of one or more dye and one or more pigment. An example of a mixture of a dye and a pigment is an indicating composition that contains a pigment that is stable to interaction with hydrogen peroxide and a dye that reacts with hydrogen peroxide. For example, a red pigment can be combined with an excess amount of blue dye to make a predominately blue chemical-indicating composition, which upon interaction with hydrogen peroxide turns pink due to bleaching of the blue dye (to colorless) by the action of hydrogen peroxide, thus revealing the red pigment. In some embodiments, the dye or pigment is chosen from methane, monoazo, diazo, triazo, diazine, thiazine, cyanine, xanthene, oxazine, anthraquinone, benzodifuranone, phthalocyanine, quinophthalone, and nitro- and nitroso colorants and combinations thereof.

An overcoat may be applied to the chemical-indicating composition. Such an overcoat may diminish or augment the reactivity of the indicating composition to sterilant gas. For example, an overcoat containing a compound capable of oxidation, such as mercaptobenzothiazole, slows the reaction of hydrogen peroxide with the indicating composition. The overcoat may also reduce the potential for transfer of the chemical-indicating composition to instruments that may contact the chemical indicator of the present disclosure before, during, or after sterilization. A number of compositions may be used as an overcoat. For example, ethylcellulose is a particularly preferred overcoat material.

The chemical-indicating composition of the present disclosure is situated in or on a chamber that is in fluid communication with the fluid pathway. The chemical-indicating composition may be placed into or onto the chamber using any convenient printing or coating method, including ink jet printing, knife coating, gravure coating, flexographic coating, etc. The chamber may be formed into the first or second sheet by removing some of the material of the sheet to provide a cutaway region, or by applying pressure at high temperature to a locus of the sheet. Alternatively, the chamber may be an entirely separate entity that may be applied to the first or second sheet using an adhesive or a lamination method. Alternatively, the chamber may be formed within the third sheet of the indicator of the present disclosure, using any convenient method including those listed above. In some embodiments, the chamber is merely a location on the first sheet, the second sheet, or the third sheet where the indicator is situated. For example, the indicator may be directly coated on or applied to a region of the first sheet, the second sheet, or the third sheet so long as it is in fluid communication with the fluid pathway. With regard to size of the chamber, the portion of the length of the fluid pathway that it occupies may be relatively small or relatively large. For example, in some embodiments of the present disclosure, the chemical-indicating composition extends the full length of the fluid pathway. What matters with regard to the chamber is that it does not adversely affect the color change of the indicator composition either by adversely affecting the flow of sterilant along the fluid pathway or by adversely affecting the color-changing characteristics of the indicator composition.

The process challenge device of the present disclosure comprises a container. The container may be fashioned from any material that is substantially impermeable to sterilant gas and that is compatible with the sterilant. For example, the container may be made of a metal such as stainless steel, a plastic such as poly(carbonate), or glass, but not of paper, for use in hydrogen peroxide sterilization. Likewise, the restriction or constriction in the process challenge device may be fashioned from a variety of materials.

EXEMPLARY EMBODIMENTS

1. A chemical indicator comprising:
    a first sheet;
    a second sheet positioned in an overlapping relationship with respect to the first sheet;
    a third sheet positioned between the first sheet and the second sheet;
    a fluid pathway; and
    a chamber;
    wherein the fluid pathway comprises a bottom portion, a top portion, and two side portions;
    wherein the chamber comprises a chemical-indicating composition;
    wherein the bottom portion of the fluid pathway is defined by the first sheet, the top portion of the fluid pathway is defined by the second sheet, and the sides of the fluid pathway are defined by the third sheet, the fluid pathway having a first end that defines a first opening and a second end that defines a second opening;
    wherein a first end of the fluid pathway is configured to be in fluid communication with ambience and the second end of the fluid pathway is configured to be in fluid communication with the chamber.
2. A chemical indicator comprising:
    a first sheet substantially impermeable to a sterilant;
    a second sheet substantially impermeable to a sterilant positioned in an overlapping relationship with respect to the first sheet;
    a third sheet positioned between the first sheet and the second sheet;
    a fluid pathway; and
    a chamber;
    wherein the fluid pathway comprises a bottom portion, a top portion, and two side portions;
    wherein the chamber comprises a chemical-indicating composition;
    wherein the bottom portion of the fluid pathway is defined by the first sheet, the top portion of the fluid pathway is defined by the second sheet, and the sides of the fluid pathway are defined by the third sheet, the fluid pathway having a first end that defines a first opening and a second end that defines a second opening;
    wherein a first end of the fluid pathway is configured to be in fluid communication with ambience and the second end of the fluid pathway is configured to be in fluid communication with the chamber.
3. A chemical indicator comprising:
    a first sheet;
    a second sheet positioned in an overlapping relationship with respect to the first sheet;
    a third sheet positioned between, and immediately adjacent to both the first sheet and the second sheet;
    a fluid pathway; and
    a chamber;
    wherein the fluid pathway comprises a bottom portion, a top portion, and two side portions;
    wherein the chamber comprises a chemical-indicating composition;
    wherein the bottom portion of the fluid pathway is defined by the first sheet, the top portion of the fluid pathway is defined by the second sheet, and the sides of the fluid pathway are defined by the third sheet, the fluid pathway having a first end that defines a first opening and a second end that defines a second opening;

wherein a first end of the fluid pathway is configured to be in fluid communication with ambience and the second end of the fluid pathway is configured to be in fluid communication with the chamber.

4. A chemical indicator comprising:
a first sheet;
a second sheet positioned in an overlapping relationship with respect to the first sheet;
a third sheet positioned between the first sheet and the second sheet;
a first adhesive layer between, and immediately adjacent to both, the first and third sheets;
a second adhesive layer between, and immediately adjacent to both, the second and third sheets;
a fluid pathway; and
a chamber;
wherein the fluid pathway comprises a bottom portion, a top portion, and two side portions;
wherein the chamber comprises a chemical-indicating composition;
wherein the bottom portion of the fluid pathway is defined by the first sheet, the top portion of the fluid pathway is defined by the second sheet, and the sides of the fluid pathway are defined by the third sheet, the fluid pathway having a first end that defines a first opening and a second end that defines a second opening;
wherein a first end of the fluid pathway is configured to be in fluid communication with ambience and the second end of the fluid pathway is configured to be in fluid communication with the chamber.

5. A chemical indicator comprising:
a first sheet;
a second sheet positioned in an overlapping relationship with respect to the first sheet;
a third sheet positioned between the first sheet and the second sheet;
a first fluid pathway;
a second fluid pathway; and
a chamber;
wherein each of the first and second fluid pathways comprises a bottom portion, a top portion, and two side portions;
wherein the chamber comprises a chemical-indicating composition;
wherein the bottom portion of each of the first and second fluid pathways is defined by the first sheet, the top portion of each of the first and second fluid pathways is defined by the second sheet, and the sides of each of the first and second fluid pathways are defined by the third sheet, each of the first and second fluid pathways having a first end that defines a first opening and a second end that defines a second opening;
wherein the first end of the first fluid pathway is configured to be in fluid communication with ambience and the second end of the first fluid pathway is configured to be in fluid communication with the chamber;
wherein the first end of the second fluid pathway is configured to be in fluid communication with the chamber and the second end of the second fluid pathway is configured to be in fluid communication with ambience, and
wherein the chamber is in fluid communication with ambience only via the first opening of the first fluid pathway and the second opening of the second fluid pathway.

6. A chemical indicator comprising:
a first sheet substantially impermeable to a sterilant;
a second sheet positioned in an overlapping relationship with respect to the first sheet;
a third sheet substantially impermeable to a sterilant positioned between the first sheet and the second sheet;
a first fluid pathway;
a second fluid pathway; and
a chamber;
wherein each of the first and second fluid pathways comprises a bottom portion, a top portion, and two side portions;
wherein the chamber comprises a chemical-indicating composition;
wherein the bottom portion of each of the first and second fluid pathways is defined by the first sheet, the top portion of each of the first and second fluid pathways is defined by the second sheet, and the sides of each of the first and second fluid pathways are defined by the third sheet, each of the first and second fluid pathways having a first end that defines a first opening and a second end that defines a second opening;
wherein the first end of the first fluid pathway is configured to be in fluid communication with ambience and the second end of the first fluid pathway is configured to be in fluid communication with the chamber;
wherein the first end of the second fluid pathway is configured to be in fluid communication with the chamber and the second end of the second fluid pathway is configured to be in fluid communication with ambience, and
wherein the chamber is in fluid communication with ambience only via the first opening of the first fluid pathway and the second opening of the second fluid pathway.

7. A chemical indicator comprising:
a first sheet;
a second sheet positioned in an overlapping relationship with respect to the first sheet;
a third sheet positioned between, and immediately adjacent to both, the first sheet and the second sheet;
a first fluid pathway;
a second fluid pathway; and
a chamber;
wherein each of the first and second fluid pathways comprises a bottom portion, a top portion, and two side portions;
wherein the chamber comprises a chemical-indicating composition;
wherein the bottom portion of each of the first and second fluid pathways is defined by the first sheet, the top portion of each of the first and second fluid pathways is defined by the second sheet, and the sides of each of the first and second fluid pathways are defined by the third sheet, each of the first and second fluid pathways having a first end that defines a first opening and a second end that defines a second opening;
wherein the first end of the first fluid pathway is configured to be in fluid communication with ambience and the second end of the first fluid pathway is configured to be in fluid communication with the chamber;

wherein the first end of the second fluid pathway is configured to be in fluid communication with the chamber and the second end of the second fluid pathway is configured to be in fluid communication with ambience, and wherein the chamber is in fluid communication with ambience only via the first opening of the first fluid pathway and the second opening of the second fluid pathway.

8. A chemical indicator comprising:
a first sheet;
a second sheet positioned in an overlapping relationship with respect to the first sheet;
a third sheet positioned between the first sheet and the second sheet;
a first adhesive layer between, and immediately adjacent to both, the first and third sheets;
a second adhesive layer between, and immediately adjacent to both, the second and third sheets;
a first fluid pathway;
a second fluid pathway; and
a chamber;
wherein each of the first and second fluid pathways comprises a bottom portion, a top portion, and two side portions;
wherein the chamber comprises a chemical-indicating composition;
wherein the bottom portion of each of the first and second fluid pathways is defined by the first sheet, the top portion of each of the first and second fluid pathways is defined by the second sheet, and the sides of each of the first and second fluid pathways are defined by the third sheet, each of the first and second fluid pathways having a first end that defines a first opening and a second end that defines a second opening;
wherein the first end of the first fluid pathway is configured to be in fluid communication with ambience and the second end of the first fluid pathway is configured to be in fluid communication with the chamber;
wherein the first end of the second fluid pathway is configured to be in fluid communication with the chamber and the second end of the second fluid pathway is configured to be in fluid communication with ambience, and
wherein the chamber is in fluid communication with ambience only via the first opening of the first fluid pathway and the second opening of the second fluid pathway.

9. A flat-format sterilization process challenge device comprising:
a container comprising a chemical indicator, wherein the chemical indicator comprises:
a chamber comprising a chemical-indicating composition;
a first sheet;
a second sheet positioned in an overlapping relationship with respect to the first sheet;
a third sheet positioned between the first sheet and the second sheet, the third sheet including a cutaway region to define a first fluid pathway,
a second fluid pathway between ambiance and the chemical indicator,
wherein the first fluid pathway is defined by the first sheet, the second sheet and the third sheet, the fluid pathway including a first opening and a second opening;
wherein the first opening provides fluid communication with the interior of the container;
wherein the second opening of the first fluid pathway is in fluid communication with the chamber, such that the chamber is in fluid communication with the interior of the container only via the first opening of the fluid pathway.

10. A flat-format sterilization process challenge device comprising:
a container comprising a chemical indicator, wherein the chemical indicator comprises:
a chamber comprising a chemical-indicating composition;
a first sheet;
a second sheet positioned in an overlapping relationship with respect to the first sheet;
a third sheet positioned between the first sheet and the second sheet, the third sheet including a cutaway region to define a first fluid pathway,
a second fluid pathway between ambiance and the chemical indicator,
wherein the first fluid pathway is defined by the first sheet, the second sheet and the third sheet, the first fluid pathway having a length L of no greater than 10 cm and including a first opening and a second opening;
wherein the first opening provides fluid communication with the interior of the container and has a width W, a height H, and an aspect ratio W/H of width to height of at least 4 (4:1);
wherein the second opening of the first fluid pathway is in fluid communication with the chamber, such that the chamber is in fluid communication with the interior of the container only via the first opening of the fluid pathway.

11. A flat-format sterilization process challenge device comprising:
a container comprising a chemical indicator, wherein the chemical indicator comprises:
a chamber comprising a chemical-indicating composition;
a first sheet;
a second sheet positioned in an overlapping relationship with respect to the first sheet;
a third sheet positioned between, and immediately adjacent to both, the first sheet and the second sheet, the third sheet including a cutaway region to define a first fluid pathway,
wherein the first fluid pathway is defined by the first sheet, the second sheet and the third sheet, the first fluid pathway having a length L of no greater than 10 cm and including a first opening and a second opening;
a second fluid pathway between ambiance and the chemical indicator,
wherein the first opening provides fluid communication with the interior of the container and has a width W, a height H, and an aspect ratio W/H of width to height of at least 4 (4:1);
wherein the second opening of the fluid pathway is in fluid communication with the chamber, such that the chamber is in fluid communication with the interior of the container only via the first opening of the fluid pathway.

12. A flat-format sterilization process challenge device comprising:
    a container comprising a chemical indicator, wherein the chemical indicator comprises:
    a chamber comprising a chemical-indicating composition;
    a first sheet;
    a second sheet positioned in an overlapping relationship with respect to the first sheet;
    a third sheet positioned between the first sheet and the second sheet, the third sheet including a cutaway region to define a first fluid pathway,
    a first adhesive layer between, and immediately adjacent to both, the first and third sheets;
    a second adhesive layer between, and immediately adjacent to both, the second and third sheets;
    wherein the first fluid pathway is defined by the first sheet, the second sheet and the third sheet, the first fluid pathway having a length L of no greater than 10 cm and including a first opening and a second opening;
    wherein the first opening provides fluid communication with the interior of the container and has a width W, a height H, and an aspect ratio W/H of width to height of at least 4 (4:1);
    wherein the second opening of the fluid pathway is in fluid communication with the chamber, such that the chamber is in fluid communication with the interior of the container only via the first opening of the fluid pathway.
    wherein the second opening of the first fluid pathway is in fluid communication with the chamber, such that the chamber is in fluid communication with the interior of the container only via the first opening of the fluid pathway.

13. A method of monitoring a sterilization process comprising:
    placing a chemical indicator according to any of the preceding embodiments into a sterilization chamber, carrying out the sterilization process,
    analyzing the chemical indicator to determine whether the sterilization process was successful.

14. The chemical indicator according to any of the preceding embodiments, wherein the first and third sheets are combined into a single monolithic layer.

15. The chemical indicator according to any of the preceding embodiments, wherein the second and third sheets are combined into a single monolithic layer.

16. The chemical indicator according to any of the preceding embodiments, wherein only one fluid pathway communicates the chamber with ambience.

17. The chemical indicator according to any of the preceding embodiments, wherein each of the first fluid pathway, and the second fluid pathway, if present, has a length L of no greater than 10 cm.

18. The chemical indicator according to any of the preceding embodiments, wherein the first opening of the fluid pathway provides fluid communication with the interior of the container and has a width W, a height H, and an aspect ratio W/H of width to height of at least 4 (4:1).

19. The chemical indicator according to any of the preceding embodiments, wherein at least one of the first fluid pathway, or the second fluid pathway, if present, is linear.

20. The chemical indicator according to any of the preceding embodiments, wherein each of the first fluid pathway, and the second fluid pathway, if present, includes a channel having a length, a width, and a height, and wherein the width and height of at least a portion of the channel define the width and height of the opening of the fluid pathway.

21. The chemical indicator according to any of the preceding embodiments, wherein the chamber is defined by a cutaway region of the third sheet.

22. The chemical indicator according to any of the preceding embodiments, wherein the chamber is located substantially centrally between the two openings.

23. The chemical indicator according to any of the preceding embodiments, wherein the chamber is defined to be that portion of a fluid pathway that comprises the chemical-indicating composition.

24. The chemical indicator according to any of the preceding embodiments, wherein the chamber has a substantially circular shape.

25. The chemical indicator according to any of the preceding embodiments, wherein the chamber has the same shape as the bottom portion of the fluid pathway.

26. The chemical indicator according to any of the preceding embodiments, wherein the chamber is a portion along the length of the fluid pathway.

27. The chemical indicator according to any of the preceding embodiments, wherein the chamber has portion that is substantially circular shape and a portion that is substantially rectangular.

28. The chemical indicator according to any of the preceding embodiments, wherein the chamber extends substantially along the entire length of the first fluid pathway and/or the second fluid pathway, if present.

29. The chemical indicator according to any of the preceding embodiments, wherein the chamber extends substantially along the entire length of the first fluid pathway and/or the second fluid pathway, if present, and wherein the chemical indicating composition is present substantially on the entire length of the chamber.

30. The chemical indicator according to any of the preceding embodiments, further comprising a second fluid pathway positioned to connect the chamber to ambience.

31. The chemical indicator according to any of the preceding embodiments, wherein a fluid pathway is configured to allow a sterilant to move along the fluid pathway in a plane parallel to a plane defined by the first sheet and the second sheet.

32. The chemical indicator according to any of the preceding embodiments, wherein the fluid pathway extends from a first edge of the first sheet and the second sheet to a second edge of the first sheet and the second sheet.

33. The chemical indicator according to any of the preceding embodiments, wherein the chemical indicator is adhered to at least one of the first sheet and the second sheet.

34. The chemical indicator according to any of the preceding embodiments, wherein the chemical indicator is in contact with at least one of the first sheet and the second sheet.

35. The chemical indicator according to any of the preceding embodiments, further comprising a barrier material in the fluid pathway to modulate the flow of sterilant.
36. The chemical indicator according to any of the preceding embodiments, wherein one or both of the first sheet and the second sheet are substantially impermeable to a sterilant.
37. A process challenge device comprising one or more chemical indicators according to any of the preceding embodiments, wherein the chemical indicator is in a container comprising an additional fluid pathway that provides fluid communication between ambience and the container.
38. A process challenge device comprising one or more chemical indicators according to any of the preceding embodiments, wherein the chemical indicator is in a container comprising an additional fluid pathway that provides fluid communication between ambience and the container, wherein the additional fluid pathway is configured to modulate the flow of the sterilant into the chemical indicator.
39. The flat-format sterilization process challenge device according to any of the preceding embodiments directed to process challenge devices, wherein one or both of the first sheet and the second sheet are substantially impermeable to a sterilant.
40. The flat-format sterilization process challenge device according to any of the preceding embodiments directed to process challenge devices, wherein the first sheet and the second sheet are substantially less permeable to the sterilant than the fluid pathway.
41. The flat-format sterilization process challenge device according to any of the preceding embodiments directed to process challenge devices, wherein the flow rate of the sterilant through the fluid pathway is greater than five times the flow rate of the sterilant through the first sheet and the second sheet.
42. The flat-format sterilization process challenge device according to any of the preceding embodiments directed to process challenge devices, wherein the length of the fluid pathway and the aspect ratio of the opening are dimensioned to provide restriction of the transport of a sterilant (by flow, diffusion, etc.) to reach the chemical-indicating composition to mimic a medical device lumen.
43. The flat-format sterilization process challenge device according to any of the preceding embodiments directed to process challenge devices, wherein the chemical indicator is positioned centrally with respect to the length of the additional fluid pathway to simulate sterilizing the locations of the medical device lumen located farthest from ambience.
44. The chemical indicator of any of the preceding embodiments, wherein the fluid pathway is configured to restrict the transport of a sterilant (by flow, diffusion, etc.) to reach the chemical-indicating composition for a given sterilization process.
45. The chemical indicator of any of the preceding embodiments, wherein the chemical-indicating composition is configured to change color in response to exposure to a given dose of sterilant.
46. The chemical indicator of any of the preceding embodiments, wherein the first sheet, the second sheet, and the third sheet are formed of a polymeric material.
47. The chemical indicator of any of the preceding embodiments, wherein the sterilant is chosen from hydrogen peroxide, steam, and ethylene oxide.
48. The chemical indicator of any of the preceding embodiments, wherein the chemical indicator is configured to monitor sterilization processes that occur at a temperature of no greater than 135 degrees C.
49. An array of chemical indicators comprising two or more chemical indicators according to any of the preceding embodiments.
50. An array of chemical indicators according to any of the preceding embodiments directed to arrays, where the fluid pathway for each of the chemical indicators modulates the flow of sterilant in a manner different from one other.

EXAMPLES

General Method for Preparation of Hydrogen Peroxide Indicators

An 8-inch width piece of clear, untreated poly(ethylene terephthalate) (PET) film (7 mil thickness) was attached to a flat surface using adhesive tape. Then, one liner of a 25-inch length of 6-inch width transfer tape (3M™ 9996 Transfer Adhesive Tape) was removed and the adhesive side of the transfer tape was carefully placed onto the PET film in a manner that minimized bubble formation between the adhesive layer and the film. (In some examples, as noted below, 3M™ 9965 Double-Coated Polyester Diagnostic Tape was placed onto the PET film in place of 3M™ 9996 Transfer Adhesive Tape.) A roller was then used to remove any bubbles that may have formed. The process was repeated to adhere a piece of the transfer adhesive tape to the other surface of the PET film. Then, the double-coated PET film was carefully trimmed to a length of 23 inches and a width of 6 inches. An Epilog Mini/Helix Model 8000 high power 50 watt $CO_2$ laser engraver was used to cut either 60 indicator frames of 2-inch length and 0.78-inch width outside dimensions or 30 indicator frames of 4-inch length and 0.78-inch width outside dimensions from the PET/adhesive construction. Each frame contained a 5-mm width cutaway through all the layers of the PET/adhesive construction running centrally along the greatest dimension of the frame. (The cutaway portion of the construction serves as the sides of the fluid pathway in the indicator.) Next, one of the liners of the PET/adhesive construction/indicator frame was removed, and the indicator frame was then pressed into place, using the adhesive of the indicator frame, onto a stripe coating of chemical-indicating composition that had been coated onto either a poly(styrene) or polyester substrate. (The placement of the indicator frame onto the stripe coating was done so that the chemical-indicating composition was contained within the nascent fluid pathway.) The other liner of the indicator frame construction was then removed and replaced using untreated 3 mil thickness PET or biaxially oriented poly(propylene) film (BOPP), which formed the top of the fluid pathway. The edges of the indicator were trimmed to remove excess film and adhesive, and one or both ends of the indicator were cut to provide one or more opening(s) of the fluid pathway to ambience. The fluid pathway height of the indicator construction was 9 mils.

To prepare indicator constructions with fluid pathway heights greater than 9 mils, thicker PET films (e.g., 5 mil PET films) or more PET/adhesive construction layers are used in construction of the indicator.

The chemical-indicating composition coated onto a substrate that was used in some of the examples was an indicator stripe that had been cut from a 3M Comply Hydrogen Peroxide Chemical Indicator 1248. Alternatively, some examples, as noted below, used the chemical-indicating composition of 3M Comply Hydrogen Peroxide Chemical Indicator 1248 that was prepared in liquid form and stripe coated onto a substrate. Suitable substrates include polyester and polystyrene films. In all the examples wherein 3M Comply Hydrogen Peroxide Chemical Indicator 1248 was used in the construction of the indicator, and in some examples, as noted below, wherein the chemical-indicating composition in liquid form was coated onto a substrate, the dry coated chemical-indicating composition was overcoated with a 13% w/w solution of ethyl cellulose in methanol and then dried at 70° C. for 5 minutes.

To prepare the indicating composition used in the examples in liquid form, the following procedure was followed:

Step 1: Red Premix: Shellac (81.8 grams) was combined with 6.8 grams of Quindo Red 19 (available from Sun Chemical, Cincinnati, Ohio) and 11.4 grams of 2-propanol and milled overnight using glass marbles in a glass jar on a ball roll mill.

Step 2: Separately, 70 grams of shellac, 22.9 grams of Rhoplex 1-545 (available from Dow Chemical, Midland, Mich.), 2.3 grams of triethanolamine (available from Sigma Aldrich, St. Louis, Mo.), and 0.6 gram Alkali Blue 6B (available from Sigma Aldrich, St. Louis, Mo.) were combined.

Step 3: The blue mixture from step 2 was combined with 4.2 grams of the Red Premix from step 1. The mixture was mixed overnight by rolling on a roller mixer.

Step 4: The resulting chemical-indicating composition was coated onto untreated poly(styrene) film, in some examples, or onto untreated polyester film, in other examples, using a #8 Meyer Bar and then dried in an oven at 80° C. for 5 minutes.

General Method of Testing Hydrogen Peroxide Indicators

Hydrogen Peroxide Indicators were prepared, as described above, and tested for color change from blue to pink upon exposure to hydrogen peroxide using a Sterrad® 100S hydrogen peroxide sterilization system (available from ASP, Irvine, Calif.). After exposure of the indicators to hydrogen peroxide using a 100S sterilization cycle, the indicators were removed from the sterilizer, placed onto a sheet of paper or film, and scanned using a photocopier using the following settings: JPEG image, 300 dpi resolution, and medium-quality color output. The resulting images were then subjected to image analysis using Image J software—a public-domain, Java-based image processing program. Using the program, each color image was first split into the corresponding red, blue, and green color components (channels). Only the red component of the image was further analyzed. The red intensity value of each image was plotted versus distance [Red Intensity; (0-255) vs. Distance (inches)] from each end of the indicator using Excel software (available from Microsoft, Seattle, Wash.). Low values of Red Intensity correspond to low exposure of the chemical-indicating composition to hydrogen peroxide (corresponding to dark regions of the strip image shown in FIGS. 10-14), whereas high values of Red Intensity correspond to high exposure of the chemical-indicating composition to hydrogen peroxide (corresponding to light regions of the strip image shown in FIGS. 10-14). A Red Intensity value greater than about 200 corresponds to redness of the chemical-indicating composition that is typically attained by full exposure to $H_2O_2$ vapor. A Red Intensity value lower than about 50 corresponds to blueness of the chemical-indicating composition that is typically attained by very little exposure to $H_2O_2$ vapor.

Example 1

Figure 10:
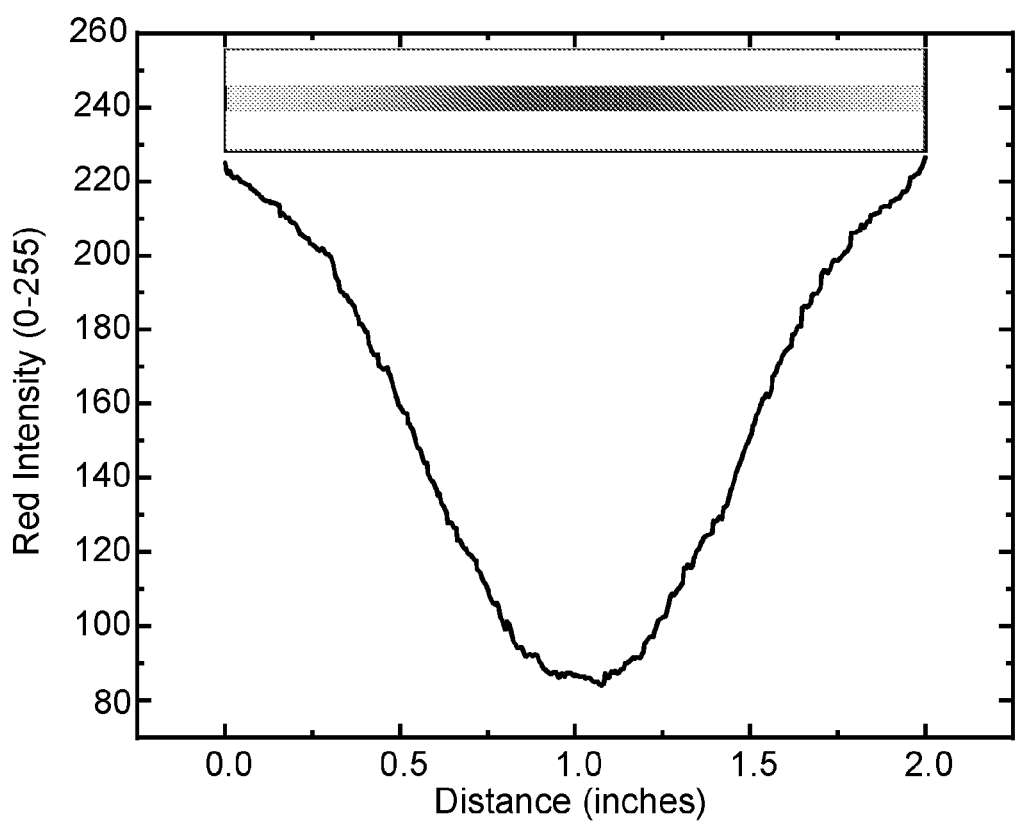
FIG. 10 is a plot showing the extent to which a chemical indicator of this disclosure changed color under a given hydrogen peroxide sterilization condition. The start of the distance measured ("0.0 inches") corresponds to one open end of the indicator. The end of the distance measured ("2.0 inches") corresponds to the other open end of the indicator.

Two-inch long hydrogen peroxide indicators were prepared, as described above, using one layer of a PET/adhesive construction (one layer of 7-mil untreated PET film laminated on each side with 1 mil thick 3M™ 9996 Transfer Adhesive Tape) and using an indicator stripe prepared by coating the chemical-indicating composition of 3M Comply Hydrogen Peroxide Chemical Indicator 1248 as described above. The resulting fluid pathway height was 9 mils. Both ends of the indicator were cut to provide an opening to ambience at both ends. The indicators were subjected to exposure to hydrogen peroxide vapor using a Sterrad® 100S sterilizer using the standard "100S" sterilization cycle. The results of the experiments are shown in FIG. 10. The results indicate that the central region of the indicator changed color from blue to pink, but not to the extent of the color change at the two ends of the indicator, thus demonstrating successful monitoring of the sterilization process.

Example 2

Figure 11:
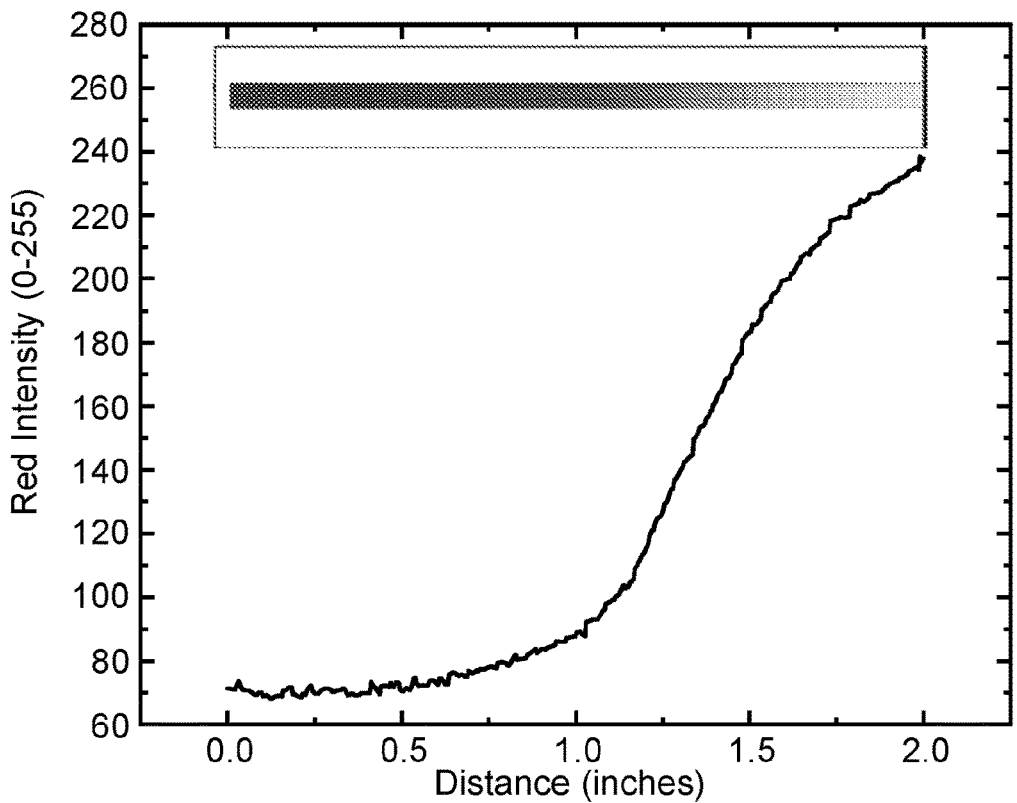
FIG. 11 is a plot showing the extent to which another chemical indicator of this disclosure changed color under a given hydrogen peroxide sterilization condition. The start of the distance measured ("0.0 inches") corresponds to the closed end of the indicator.

Two-inch long hydrogen peroxide indicators were prepared, as described above, using one layer of a PET/adhesive construction (one layer of 7-mil untreated PET film laminated on each side with 1 mil thick 3M™ 9996 Transfer Adhesive Tape) and using an indicator stripe prepared by coating the chemical-indicating composition of 3M Comply Hydrogen Peroxide Chemical Indicator 1248 as described above. The resulting fluid pathway height was 9 mils. One end of the indicator was cut to provide an opening to ambience at one end. The indicators were subjected to exposure to hydrogen peroxide vapor using a Sterrad® 100S sterilizer using the standard "100S" sterilization cycle. The results of the experiments are shown in FIG. 11. The results indicate that the region of the indicator proximal to the opening of the indicator changed color from blue to pink, that the region of the indicator proximal to the closed end of the indicator remained relatively blue, and that the central region of the indicator showed some pink color, but not as much pink as the region of the indicator proximal to the opening of the indicator, thus demonstrating successful monitoring of the sterilization process.

Example 3

Figure 12:
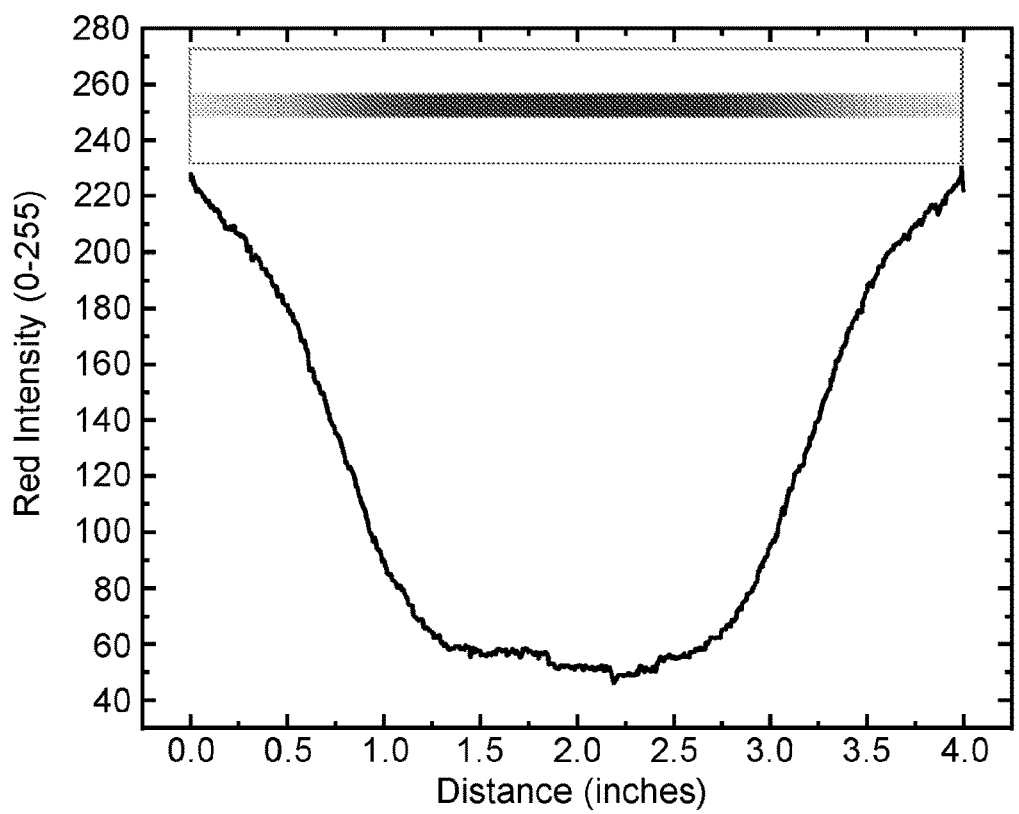
FIG. 12 is a plot showing the extent to which another chemical indicator of this disclosure changed color under a given hydrogen peroxide sterilization condition. The start of the distance measured ("0.0 inches") corresponds to one open end of the indicator. The end of the distance measured ("4.0 inches") corresponds to the other open end of the indicator.

Four-inch long hydrogen peroxide indicators were prepared, as described above, using one layer of a PET/adhesive construction (one layer of 7-mil untreated PET film laminated on each side with 1 mil thick 3M™ 9996 Transfer Adhesive Tape) and using an indicator stripe prepared by coating the chemical-indicating composition of 3M Comply Hydrogen Peroxide Chemical Indicator 1248 as described above. The resulting fluid pathway height was 9 mils. Both ends of the indicator were cut to provide an opening to ambience at both ends. The indicators were subjected to exposure to hydrogen peroxide vapor using a Sterrad® 100S sterilizer using the standard "100S" sterilization cycle. The results of the experiments are shown in FIG. 12. The results indicate that the central region of the indicator had minimal color change from blue, whereas the color changed from blue to pink at the two ends of the indicator, thus demonstrating successful monitoring of the sterilization process.

Example 4

Figure 13:
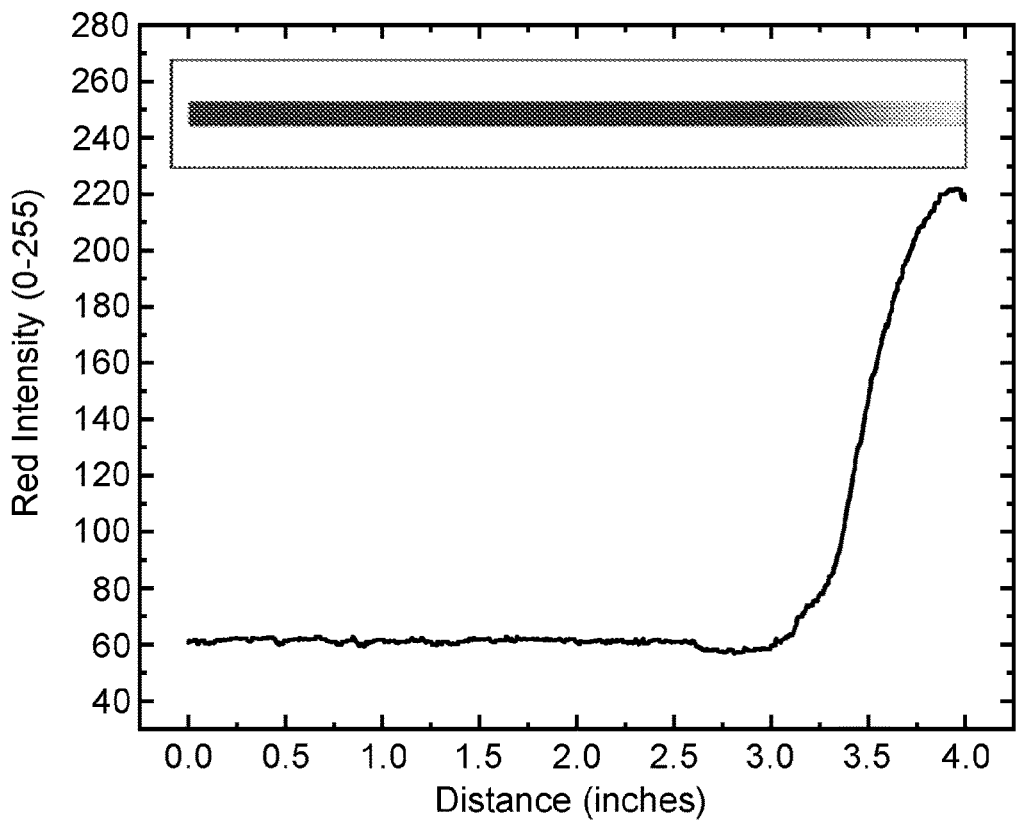
FIG. 13 is a plot showing the extent to which another chemical indicator of this disclosure changed color under a given hydrogen peroxide sterilization condition. The start of the distance measured ("0.0 inches") corresponds to the closed end of the indicator.

Four-inch long hydrogen peroxide indicators were prepared, as described above, using one layer of a PET/adhesive construction (one layer of 7-mil untreated PET film laminated on each side with 1 mil thick 3M™ 9996 Transfer Adhesive Tape) and using an indicator stripe prepared by coating the chemical-indicating composition of 3M Comply Hydrogen Peroxide Chemical Indicator 1248 as described above. The resulting fluid pathway height was 9 mils. One end of the indicator was cut to provide an opening to ambience at one end. The indicators were subjected to exposure to hydrogen peroxide vapor using a Sterrad® 100S sterilizer using the standard "100S" sterilization cycle. The results of the experiments are shown in FIG. 13. The results indicate that the region of the indicator proximal to the opening of the indicator changed color from blue to pink, that the region of the indicator proximal to the closed end of the indicator remained relatively blue, and that the central region of the indicator showed minimal color change from blue, thus demonstrating successful monitoring of the sterilization process.

Examples 5-48

Examples 5-48 demonstrate the indicator's performance as a function of several construction variables listed in the table below. The indicators were subjected to exposure to hydrogen peroxide vapor using a Sterrad® 100S sterilizer. Performance is characterized using three different responses. Delta Red Intensity is the difference in the red intensity between the open end and the closed end of the indicator fluid pathway. Delta Red Intensity values can range from 0 to 255 and is a measurement of the blue/red color contrast. A large value of Delta Red Intensity indicates a large difference in the blue/red color balance when comparing the ends of the indicator fluid pathway. Vmax Red is the maximum value of the first derivative of the Red Intensity profile across the length of the indicator fluid pathway. A large value of Vmax Red Intensity indicates a sharp transition from blue to red across the moving front of the indicator. Front Location is the position of the indicator's moving front and corresponds to the location along the indicator's fluid pathway (measured from the open end) where Vmax Red Intensity is observed. Front Location is also provided as a percentage of the total length of the indicator strip. Although all the indicators exemplified here represent useful constructions, some of them are preferred. Indicator constructions that result in Delta Red Intensity values greater than 130, Vmax Red Intensity greater than 0.5, Front Location greater than 10 mm or, alternatively, greater than 20% of the total indicator strip length, are preferred.

| | | Indicator Construction Variable | | | | | | Performance Response | | | |
|---|---|---|---|---|---|---|---|---|---|---|---|
| Example | Length of Indicator (inches) | Thickness of untreated PET film used as Sheet 3 | Sheet 1 material (substrate) | Sheet 2 material (top film) | Resulting height of fluid pathway (mils) | Single-end or double-end opening | Overcoat applied to ink? | Ink Coating Thickness (Meyer Rod #) | Delta Red Intensity (0-255) | Vmax Red Intensity (AU) | Front Location (mm) | Front Location (%) |
| 5 | 2 | 7 | 1248 | PET | 9 | SE | Y | 8 | 180 | 0.62 | — | — |
| 6 | 2 | 7 | 1248 | PET | 9 | SE | N | 8 | 62 | 0.20 | — | — |
| 7 | 2 | 7 | 1248 | SBOPP | 9 | SE | Y | 8 | 132 | 0.78 | — | — |
| 8 | 2 | 7 | 1248 | SBOPP | 9 | SE | N | 8 | 43 | 0.11 | — | — |
| 9 | 2 | 7 | 1248 | PET | 9 | SE | Y | 22 | 143 | 0.63 | — | — |
| 10 | 2 | 7 | 1248 | PET | 9 | SE | N | 22 | 111 | 0.41 | — | — |
| 11 | 2 | 7 | 1248 | SBOPP | 9 | SE | Y | 22 | 128 | 0.65 | — | — |
| 12 | 2 | 7 | 1248 | SBOPP | 9 | SE | N | 22 | 93 | 0.31 | — | — |
| 13 | 2 | 7 | 1295 | PET | 9 | SE | Y | 8 | 164 | 0.96 | — | — |
| 14 | 2 | 7 | 1295 | PET | 9 | SE | N | 8 | 124 | 0.44 | — | — |
| 15 | 2 | 7 | 1295 | SBOPP | 9 | SE | Y | 8 | 147 | 0.78 | — | — |
| 16 | 2 | 7 | 1295 | SBOPP | 9 | SE | N | 8 | 113 | 0.39 | — | — |
| 17 | 2 | 7 | 1295 | PET | 9 | SE | Y | 22 | 172 | 1.12 | — | — |
| 18 | 2 | 7 | 1295 | PET | 9 | SE | N | 22 | 137 | 0.45 | — | — |
| 19 | 2 | 7 | 1295 | SBOPP | 9 | SE | Y | 22 | 153 | 0.73 | — | — |
| 20 | 2 | 7 | 1295 | SBOPP | 9 | SE | N | 22 | 132 | 0.71 | — | — |
| 21 | 2 | 7 | 1248 | PET | 9 | DE | Y | 8 | 61 | 0.26 | — | — |
| 22 | 2 | 7 | 1248 | PET | 9 | DE | N | 8 | 18 | 0.05 | — | — |
| 23 | 2 | 7 | 1248 | SBOPP | 9 | DE | Y | 8 | 70 | 0.33 | — | — |
| 24 | 2 | 7 | 1248 | SBOPP | 9 | DE | N | 8 | 10 | 0.04 | — | — |
| 25 | 2 | 7 | 1248 | PET | 9 | DE | Y | 22 | 77 | 0.45 | — | — |
| 26 | 2 | 7 | 1248 | PET | 9 | DE | N | 22 | 15 | 0.12 | — | — |
| 27 | 2 | 7 | 1248 | SBOPP | 9 | DE | Y | 22 | 59 | 0.38 | — | — |
| 28 | 2 | 7 | 1248 | SBOPP | 9 | DE | N | 22 | 33 | 0.14 | — | — |
| 29 | 2 | 7 | 1295 | PET | 9 | DE | Y | 8 | 77 | 0.47 | — | — |
| 30 | 2 | 7 | 1295 | PET | 9 | DE | N | 8 | 52 | 0.21 | — | — |
| 31 | 2 | 7 | 1295 | SBOPP | 9 | DE | Y | 8 | 78 | 0.50 | — | — |
| 32 | 2 | 7 | 1295 | SBOPP | 9 | DE | N | 8 | 18 | 0.12 | — | — |
| 33 | 2 | 7 | 1295 | PET | 9 | DE | Y | 22 | 97 | 0.64 | — | — |
| 34 | 2 | 7 | 1295 | PET | 9 | DE | N | 22 | 45 | 0.19 | — | — |
| 35 | 2 | 7 | 1295 | SBOPP | 9 | DE | Y | 22 | 68 | 0.48 | — | — |
| 36 | 2 | 7 | 1295 | SBOPP | 9 | DE | N | 22 | 35 | 0.13 | — | — |
| 37 | 2 | 7 | 1248 | PET | 9 | SE | Y | 8 | 160 | 0.81 | 17.4 | 34 |
| 38 | 2 | 10 | 1248 | PET | 12 | SE | Y | 8 | 145 | 0.69 | 17.8 | 35 |
| 39 | 2 | 14 | 1248 | PET | 18 | SE | Y | 8 | 143 | 0.56 | 24.0 | 47 |
| 40 | 2 | 7 | 1248 | PET | 9 | SE | Y | 22 | 175 | 1.01 | 13.8 | 27 |

-continued

| | | | | Indicator Construction Variable | | | | Performance Response | | | |
|---|---|---|---|---|---|---|---|---|---|---|---|
| Example | Length of Indicator (inches) | Thickness of untreated PET film used as Sheet 3 | Sheet 1 material (substrate) | Sheet 2 material (top film) | Resulting height of fluid pathway (mils) | Single-end or double-end opening | Overcoat applied to ink? | Ink Coating Thickness (Meyer Rod #) | Delta Red Intensity (0-255) | Vmax Red Intensity (AU) | Front Location (mm) | Front Location (%) |
| 41 | 2 | 10 | 1248 | PET | 12 | SE | Y | 22 | 178 | 0.97 | 13.2 | 26 |
| 42 | 2 | 14 | 1248 | PET | 18 | SE | Y | 22 | 177 | 0.81 | 15.6 | 31 |
| 43 | 2 | 7 | 1295 | PET | 9 | SE | Y | 8 | 181 | 1.15 | 10.9 | 21 |
| 44 | 2 | 10 | 1295 | PET | 12 | SE | Y | 8 | 159 | 0.90 | 10.9 | 21 |
| 45 | 2 | 14 | 1295 | PET | 18 | SE | Y | 8 | 165 | 0.73 | 15.1 | 30 |
| 46 | 2 | 7 | 1295 | PET | 9 | SE | Y | 22 | 197 | 1.62 | 10.5 | 21 |
| 47 | 2 | 10 | 1295 | PET | 12 | SE | Y | 22 | 179 | 1.26 | 9.5 | 19 |
| 48 | 2 | 14 | 1295 | PET | 18 | SE | Y | 22 | 165 | 1.04 | 12.3 | 24 |

Examples 49-54

Examples 49-54 demonstrate the indicator's performance as a function of different cycle types in various sterilizers as listed in the table below. The sterilizers that were used include: ASP Sterrad® 100S, ASP Sterrad® 100NX, ASP Sterrad® NX and Sterilucent PSD-85. The results indicate that the indicator can monitor hydrogen peroxide sterilization cycles for a variety of sterilizers.

| | | Indicator Construction Variable | | | | | | |
|---|---|---|---|---|---|---|---|---|
| Example | Length of Indicator (inches) | Thickness of untreated PET film used as Sheet 3 | Sheet 1 material (substrate) | Sheet 2 material (top film) | Resulting height of fluid pathway (mils) | Single-end or double-end opening | Overcoat applied to ink? | Ink Coating Thickness (Meyer Rod #) |
| 49 | 2 | 7 | 1248 | PET | 9 | SE | Y | 8 |
| 50 | 2 | 7 | 1248 | PET | 9 | SE | Y | 8 |
| 51 | 2 | 7 | 1248 | PET | 9 | SE | Y | 8 |
| 52 | 2 | 7 | 1248 | PET | 9 | SE | Y | 8 |
| 53 | 2 | 7 | 1248 | PET | 9 | SE | Y | 8 |
| 54 | 2 | 7 | 1248 | PET | 9 | SE | Y | 8 |

| | Sterilization Variables | | |
|---|---|---|---|
| Example | Sterilizer | Cycle Type | Cycle (Complete or Incomplete) |
| 49 | ASP Sterrad ® 100 s | Standard | Complete |
| 50 | ASP Sterrad ® 100NX | Standard | Complete |
| 51 | ASP Sterrad ® 100NX | Express | Complete |
| 52 | ASP Sterrad ® NX | Standard | Complete |
| 53 | ASP Sterrad ® NX | Advanced | Complete |
| 54 | Sterilucent PSD-85 | Standard | Complete |

| | Performance Response | | | |
|---|---|---|---|---|
| Example | Delta Red Intensity (0-255) | Vmax Red Intensity (AU) | Front Location (mm) | Front Location (%) |
| 49 | 170 | 1.20 | 19.3 | 38 |
| 50 | 124 | 0.62 | 40.2 | 79 |
| 51 | 197 | 2.57 | 9.3 | 18 |
| 52 | 169 | 1.30 | 27.7 | 55 |
| 53 | 108 | 0.28 | 31.7 | 62 |
| 54 | 177 | 0.97 | 35.6 | 70 |

Examples 55-60

Examples 55-60 demonstrate the indicator's ability to distinguish between complete and incomplete sterilization cycles in various sterilizers as listed in the table below. The sterilizers that were used included: ASP Sterrad® 100S and ASP Sterrad® 100NX. Incomplete cycles are equivalent to one-half of a complete cycle. Furthermore, Examples 55-58 demonstrate that the indicator can distinguish complete from incomplete cycles for different loads placed in the sterilization chamber. Load 1 corresponds to two trays of surgical steel instruments, each tray containing 10.23 lbs of instrumentation. Load 2 corresponds to two trays of surgical steel instruments, each tray containing 10.23 lbs of instrumentation. In addition, for Load 2, the tray placed on the top rack of the sterilizer also contains two protectant silicone mats (available from Advanced Sterilization Products), while the tray placed on the bottom rack of the sterilizer also contains one protectant silicone mat. The results indicate that the indicator can differentiate between complete and incomplete cycles for a variety of sterilizers using different loading conditions. For the ASP Sterrad® 100S sterilizer using Load Type 1, the front location decreased (signifying a front location closer to the indicator's fluid pathway opening) by a factor of 1.8 for an incomplete cycle. For the same sterilizer using Load Type 2, the front location decreased by a factor of 8.5 for an incomplete cycle. Finally, for the ASP Sterrad® 100NX sterilizer using Load Type 1, the front location decreased by a factor of 1.2 for an incomplete cycle.

| | Sterilization Variables | | | |
|---|---|---|---|---|
| Example | Sterilizer | Cycle Type | Load Type | Cycle (Complete or Incomplete) |
| 55 | ASP Sterrad® 100 s | Standard | 1 | Complete |
| 56 | ASP Sterrad® 100 s | Standard | 1 | Incomplete |
| 57 | ASP Sterrad® 100 s | Standard | 2 | Complete |
| 58 | ASP Sterrad® 100 s | Standard | 2 | Incomplete |
| 59 | ASP Sterrad® 100NX | Standard | 1 | Complete |
| 60 | ASP Sterrad® 100NX | Standard | 1 | Incomplete |

| | Performance Response | | | |
|---|---|---|---|---|
| Example | Delta Red Intensity (0-255) | Vmax Red Intensity (AU) | Front Location (mm) | Front Location (%) |
| 55 | 157 | 1.14 | 19.8 | 39 |
| 56 | 146 | 1.15 | 11.4 | 22 |
| 57 | 165 | 0.85 | 17.4 | 34 |
| 58 | 91 | 1.90 | 1.9 | 4 |

| | Indicator Construction Variable | | | | | | | |
|---|---|---|---|---|---|---|---|---|
| Example | Length of Indicator (inches) | Thickness of untreated PET film used as Sheet 3 | Sheet 1 material (substrate) | Sheet 2 material (top film) | Resulting height of fluid pathway (mils) | Single-end or double-end opening | Overcoat applied to ink? | Ink Coating Thickness (Meyer Rod #) |
| 55 | 2 | 7 | 1248 | PET | 9 | SE | Y | 8 |
| 56 | 2 | 7 | 1248 | PET | 9 | SE | Y | 8 |
| 57 | 2 | 7 | 1248 | PET | 9 | SE | Y | 8 |
| 58 | 2 | 7 | 1248 | PET | 9 | SE | Y | 8 |
| 59 | 2 | 7 | 1248 | PET | 9 | SE | Y | 8 |
| 60 | 2 | 7 | 1248 | PET | 9 | SE | Y | 8 |

Examples 61-63

The table below specifies the construction of each of examples 61-63. Examples 61 and 62 are control examples.

| | Indicator Construction Variable | | | | | | | |
|---|---|---|---|---|---|---|---|---|
| Example | Length of Indicator (inches) | Thickness of untreated PET film used as Sheet 3 | Sheet 1 material (substrate) | Sheet 2 material (top film) | Resulting height of fluid pathway (mils) | Single-end or double-end opening | Overcoat applied to ink? | Ink Coating Thickness (Meyer Rod #) |
| 61 | 2 | 10 | 1248 | No Sheet 2 | 12 | No openings | Y | 8 |
| 62 | 2 | 10 | 1248 | PET | 12 | No openings | Y | 8 |
| 63 | 2 | 10 | 1248 | PET | 12 | SE | Y | 8 |
| 64 | 2 | 10 | 1248 | PET | 12 | SE | Y | 8 |

Figure 14:
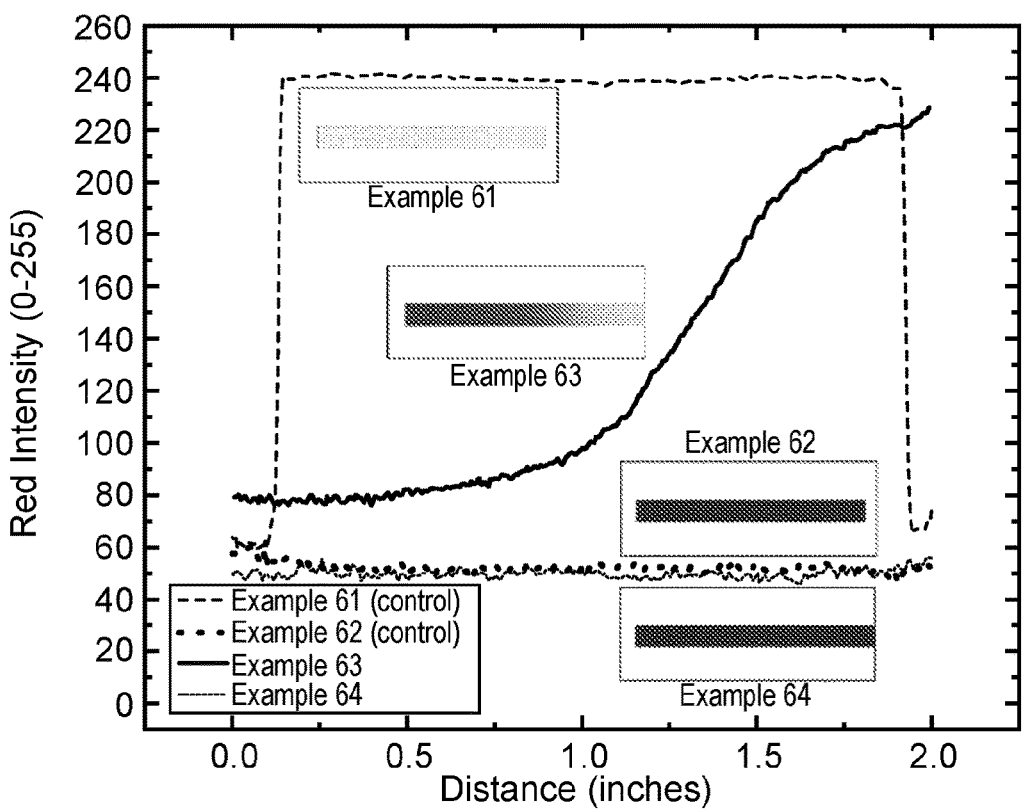
FIG. 14 is a plot showing the extent to which other chemical indicators of this disclosure changed color under a given hydrogen peroxide sterilization condition. The start of the distance measured ("0.0 inches") corresponds to one closed end of each of the indicators. The end of the distance measured ("2.0" inches) corresponds to a closed end of two of the indicators and an open end on the other two indicators.

Examples 63 and 64 are working indicators used for comparison to the two control examples 61 and 62; all examples were constructed using the method described above. Example 61 corresponds to an indicator construction identical to examples 63 and 64 with the exception that Sheet 2 is missing. Example 62 corresponds to an indicator construction identical to examples 63 and 64 with the exception that the fluid pathway is completely sealed at both ends (i.e. the indicator of example 62 has no opening in the fluid pathway). The indicator examples 61-63 were subjected to exposure to hydrogen peroxide vapor using a Sterrad® 100S sterilizer. Indicator example 64 was not exposed to a sterilization cycle. The results of the experiments are shown in FIG. 14. The results demonstrate that the comparative example 63 functioned as expected with a clear front located at approximately 30% of the total length of the indicator strip from the open end of the fluid pathway. In contrast, control example 61 has no defined front and the entire length of the indicator strip had an average Red Intensity value of 240. This indicator reached 94% of its theoretical endpoint color of Red Intensity (255) over the entire length of the indicator strip. Example 61 demonstrates that without Sheet 2 (i.e. without a defined top to the fluid pathway), the indicator does not have a moving front. For example 62, the results shown in FIG. 14 indicate that the average value of Red Intensity is 52 over the entire length of the indicator strip. This value is nearly identical to that of example 64 (average value of Red Intensity=50), which corresponds to an indicator that has not been exposed to the sterilizer. Thus, Example 62 demonstrates that when the indicator fluid pathway openings are sealed, the indicator construction is essentially impermeable to hydrogen peroxide vapor (i.e. sheets 1, 2 and 3 are impermeable to hydrogen peroxide vapor), and that exposure of the chemical-indicating composition along the indicator strip only occurs when hydrogen peroxide vapor enters the channel through the opening(s) at one or both ends of the indicator.

The invention claimed is:

1. A chemical indicator comprising:
   a first sheet substantially impermeable to a sterilant;
   a second sheet substantially impermeable to the sterilant positioned in an overlapping relationship with respect to the first sheet;
   a third sheet disposed in between the first sheet and the second sheet;
   a fluid pathway forming an open channel, the open channel defined by the first sheet forming a bottom portion of the fluid pathway, the second sheet forming a top portion of the fluid pathway, and the third sheet forming two side portions of the fluid pathway; a first end having a first opening facing out of the chemical indicator; and a second end having a second opening in fluid communication with a chamber;
   and the chamber comprising a chemical composition, wherein the chamber is defined by a cutaway region of the third sheet.

2. A flat-format sterilization process challenge device comprising: a container comprising a chemical indicator, wherein the chemical indicator comprises: a chamber comprising a chemical-indicating composition; a first sheet; a second sheet positioned in an overlapping relationship with respect to the first sheet; a third sheet disposed in between the first sheet and the second sheet, the third sheet including a cutaway region to define a first fluid pathway, a second fluid pathway between ambiance and the chemical indicator, wherein the first fluid pathway is defined by the first sheet, the second sheet, and the third sheet, and wherein the first fluid pathway including a first opening and a second opening; wherein the first opening provides fluid communication with an interior of the container; wherein the second opening of the first fluid pathway is in fluid communication with the chamber, such that the chamber is in fluid communication with the interior of the container only via the first opening of the fluid pathway.

3. The chemical indicator according to claim 1, wherein the first sheet and the third sheet are combined into a single monolithic layer.

4. The chemical indicator according to claim 1, wherein the second and third sheets are combined into a single monolithic layer.

5. The chemical indicator according to claim 1, wherein only one fluid pathway communicates the chamber with ambience.

6. The chemical indicator according to claim 1, wherein each of the first fluid pathway, and the second fluid pathway, if present, has a length L of no greater than 10 cm.

7. The chemical indicator according to claim 1, wherein the first opening of the fluid pathway provides fluid communication with an interior of the chamber and has a width W, a height H, and an aspect ratio W/H of width to height of at least 4 (4:1).

8. The chemical indicator according to claim 1, wherein the chamber is a portion along a length of the fluid pathway.

9. The chemical indicator according to claim 1, wherein the chamber extends substantially along an entire length of the first fluid pathway or the second fluid pathway, if present, and wherein the chemical indicating composition is present substantially on the entire length of the chamber.

10. The chemical indicator according to claim 1, further comprising a second fluid pathway positioned to connect the chamber to ambience.

11. The chemical indicator according to claim 1, wherein the fluid pathway is configured to allow the sterilant to move along the fluid pathway in a plane parallel to the plane defined by the first sheet and the second sheet.

12. The chemical indicator according to claim 1, further comprising a process challenge device comprising at least a chemical indicator, wherein the chemical indicator is in a container comprising an third fluid pathway that provides fluid communication between ambience and the container.

13. The chemical indicator according to claim 1, wherein an array of chemical indicators comprises two or more chemical indicators.

14. The chemical indicator according to claim 1 directed to arrays, where the fluid pathway for each of the chemical indicators modulates flow of the sterilant in a manner different from one other.

* * * * *